US00PP10044P

United States Patent [19]

Rother

[11] Patent Number: Plant 10,044

[45] Date of Patent: Sep. 30, 1997

[54] PETUNIA PLANT NAMED 'SUNLACE'

[76] Inventor: Reinhard W. Rother, 56 Emerald Monbulk Road, Emerald, Victoria 3782, Australia

[21] Appl. No.: 679,896

[22] Filed: Jul. 15, 1996

[51] Int. Cl.[6] ..... A01H 5/00

[52] U.S. Cl. ..... Plt./68.1

[58] Field of Search ..... Plt./68.1

*Primary Examiner*—James R. Feyrer
*Attorney, Agent, or Firm*—C. A. Whealy

[57] ABSTRACT

A distinct cultivar of Petunia plant named 'Sunlace', characterized by its large light violet petals with yellow green flower throat and light violet flower tube; vigorous growth habit and rapid growth rate; decumbent and spreading plant habit; freely branching habit; early flowering; very floriferous with numerous flowers per plant; and tolerance to rain, drought and temperature extremes.

2 Drawing Sheets

The present invention relates to a new and distinct cultivar of Petunia plant, botanically known as *Petunia axillaris*, and hereinafter referred to by the cultivar name 'Sunlace'.

The new cultivar is a product of a planned breeding program conducted by the inventor in Emerald, Victoria, Australia. The objective of the breeding program was to create new Petunia cultivars having large flowers, a spreading plant habit, and desirable flower colors.

The new cultivar originated from a cross made by the inventor of the inventor's proprietary Petunia selection No. 914-Z as the male or pollen parent with the inventor's proprietary Petunia selection No. S-286 as the female or seed parent.

The cultivar 'Sunlace' was discovered and selected by the inventor as a flowering plant within the progeny of the stated cross in a controlled environment in Emerald, Victoria, Australia. Asexual reproduction of the new cultivar by terminal cuttings taken at Emerald, Victoria, Australia, has shown that the unique features of this new Petunia are stable and reproduced true to type in successive generations.

The cultivar 'Sunlace' has not been observed under all possible environmental conditions. The phenotype may vary somewhat with variations in environment such as temperature and light intensity, without, however, any variance in genotype. The following observations, measurements and comparisons describe plants grown in Emerald, Victoria, Australia, under commercial production conditions.

The following traits have been repeatedly observed and are determined to be the unique characteristics of 'Sunlace'. These characteristics in combination distinguish 'Sunlace' as a new and distinct cultivar:

1. Large light violet petals with yellow green flower throat and light violet flower tube.
2. Vigorous growth habit and rapid growth rate.
3. Decumbent and spreading plant habit.
4. Freely branching habit. Plants do not require pinching.
5. Early flowering.
6. Very floriferous with numerous flowers per plant.
7. Tolerant to rain, drought and temperature extremes.

The cultivar 'Sunlace' is similar in flower color to the cultivar 'Sweet Victory' (disclosed in U.S. Plant Pat. No. 9,409). The cultivar 'Sunlace' differs from the cultivar Sweet Victory in the following characteristics:

1. Leaves of the cultivar 'Sunlace' are elliptic in shape whereas leaves of the cultivar 'Sweet Victory' are ovate in shape.
2. Leaves of the cultivar 'Sunlace' are more pubescent than leaves of the cultivar 'Sweet Victory'.
3. Internode length on plants of the cultivar 'Sunlace' is shorter than plants of the cultivar 'Sweet Victory'.
4. Flowers are larger on plants of the cultivar 'Sunlace' compared to plants of the cultivar 'Sweet Victory'.

5. Plants of the cultivar 'Sunlace' have longer sepals and sepals are elliptic than plants of the cultivar 'Sweet Victory' that has spatulate sepals.
6. Pedicels of the cultivar 'Sunlace' are thicker than pedicels of the cultivar 'Sweet Victory'.
7. The flower throat and tube color of plants of the cultivar 'Sunlace' are yellow green and light violet, respectively, whereas the flower throat and tube color of plants of the cultivar 'Sweet Victory' are dark violet.
8. The flower throat and tube vein color of plants of the cultivar 'Sunlace' are faint purple and yellow green, respectively, whereas the flower throat and tube vein color of plants of the cultivar 'Sweet Victory' is purple.
9. The inside and outside petal colors of plants of the cultivar 'Sunlace' is lighter than the inside and outside petal colors of plants of the cultivar 'Sweet Victory'.
10. The stigma is above the anthers on plants of the cultivar 'Sunlace' whereas the stigma is below the anthers on plants of the cultivar 'Sweet Victory'.
11. The anther color of plants of the cultivar 'Sunlace' is cream whereas the anther color of plants of the cultivar 'Sweet Victory' is blue.

A detailed comparison of the cultivars 'Sunlace' and 'Sweet Victory' appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical hanging basket plant of the cultivar Sunlace.

The second photograph comprises a close-up view of individual flowers of the cultivar Sunlace.

Flower and foliage colors may appear different than the actual colors due to light reflectance.

In the following description, color references are made to the Royal Horticultural Society Colour Chart except where general terms of ordinary dictionary significance are used. Measurements are averages from ten specimens selected at random from five plants.

Botanical classification: *Petunia axillaris* cultivar 'Sunlace'.

Parentage:

*Male or pollen parent.*—*Petunia axillaris,* inventor's proprietary selection No. 914-Z.

*Female or seed parent.*—*Petunia axillaris,* inventor's proprietary selection No. S-286.

Propagation:

*Type cutting.*—Terminal vegetative cuttings.

*Time to initiate roots.*—About ten days at 21C soil temperature.

*Rooting habit.*—Numerous, fine, fibrous, and well-branched.

Plant description:

*Form.*—Indeterminate, decumbent, diffuse spreading, viscid, glandular pubescent.

*Branching habit.*—Freely branching.

*Plant height.*—About 16.2 cm.

*Plant width.*—About 64.2 cm.

*Vigor.*—Vigorous.

*Crop time.*—8 to 9 weeks from a unrooted cutting to a 10.5-cm finished and flowering container.

*Foliage description.*—Leaves simple, generally symmetrical, sessile, and long persisting. Leaves at first whorled, later alternate, somewhat fleshy. Size (largest leaves): Length: About 7.9 cm. Width: About 4.4 cm. Thickness: About 1.5 mm. Shape: Elliptic. Aspect: Slanting upwards to horizontal. Apex: Acute. Base: Attenuate. Margin: Entire. Texture: Moderately pubescent. Color: Young foliage upper side: 146A to 147A. Young foliage under side: 147B. Mature foliage upper side: 146A to 147A. Mature foliage under side: 147B.

*Stem description.*—Stems upright to spreading, hirsute. Stem diameter: About 2.5 mm. Internode length: Medium, about 2.6 cm. Stem color: Green, 144A.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall in Northern Hemisphere.

*Quantity.*—Numerous flowers per plant.

*Corolla.*—Diameter: About 8.2 cm. Height: About 6.2 cm. Flower tube width at distal end: About 1.7 cm. Petal quantity: Five, fused. Petal apex: Obtuse. Margin: Entire, undulating. Texture: Pubescent on outside, smooth and satiny on inside. Color: Flower throat (inside): 150D. Flower throat vein color (inside): Faint purple. Flower tube color (outside): 76D. Flower tube vein color (outside): 144A/144B. Petal color, inside: 80C/80D. Petal color, inside, with age: Color fades to 75C/75D. Petal vein color, inside: 80C. Petal color, outside: 75A to 75D. Petal vein color, outside: 144A.

*Sepals.*—Quantity: Five. Size: Length: About 3 cm. Width: About 6.9 mm. Shape: Elliptic. Apex: Obtuse. Margin: Entire. Texture: Pubescent. Aspect: Upright. Color: Inside: 146A. Outside: 146B.

*Pedicel.*—Aspect: Upright. Size: Length: About 2.5 cm. Width: About 2.2 min. Texture: Pubescent. Color: 144A.

*Reproductive organs.*—Stigma above anthers, superior ovary. Stamens: Stamen number: Five, four are didymous. Anther color: Cream. Filament color: Green white. Pistils: Stigma color: Green. Style color: Yellow green.

Disease resistance: No known Petunia diseases observed to date.

Fruit and seed production: Rarely observed.

*Fruit.*—Capsule with two undivided valves.

*Seeds.*—Minute, spherical.

CHART A

| CHARACTERISTIC | 'SUNLACE' | 'SWEET VICTORY' |
|---|---|---|
| LEAF SHAPE | Elliptic | Ovate |
| LEAF PUBESCENCE | Moderate | Sparse to moderate |
| INTERNODE LENGTH | 2.6 cm | 3.4 cm |
| COROLLA DIAMETER | 8.2 cm | 6.6 cm |
| COROLLA HEIGHT | 6.2 cm | 5.5 cm |
| SEPAL LENGTH | 3 cm | 2.1 cm |
| SEPAL SHAPE | Elliptic | Spatulate |
| PEDICEL WIDTH | 2.2 cm | 1.6 cm |
| FLOWER THROAT COLOR | 150D | 83C/83D |
| FLOWER THROAT VEIN COLOR | Faint purple | Purple |
| FLOWER TUBE COLOR, OUTSIDE | 76D | 83C |
| FLOWER TUBE VEIN COLOR, OUTSIDE | Yellow green | Purple |
| PETAL COLOR, INSIDE | 80C/80D | 80A |
| PETAL VEIN COLOR, INSIDE | Red purple | Red purple |
| PETAL COLOR, OUTSIDE | 75A to 75D | 84B |
| PETAL VEIN COLOR, OUTSIDE | Yellow green | Red purple |
| PETAL TIP | Medium to obverse | Obverse |
| STIGMA RELATIVE TO ANTHERS | Above | Below |
| ANTHER COLOR | Cream | Blue |
| FILAMENT COLOR | Green white | Green white with violet towards anther |

It is claimed:

1. A new and distinct cultivar of Petunia plant named 'Sunlace', as illustrated and described.

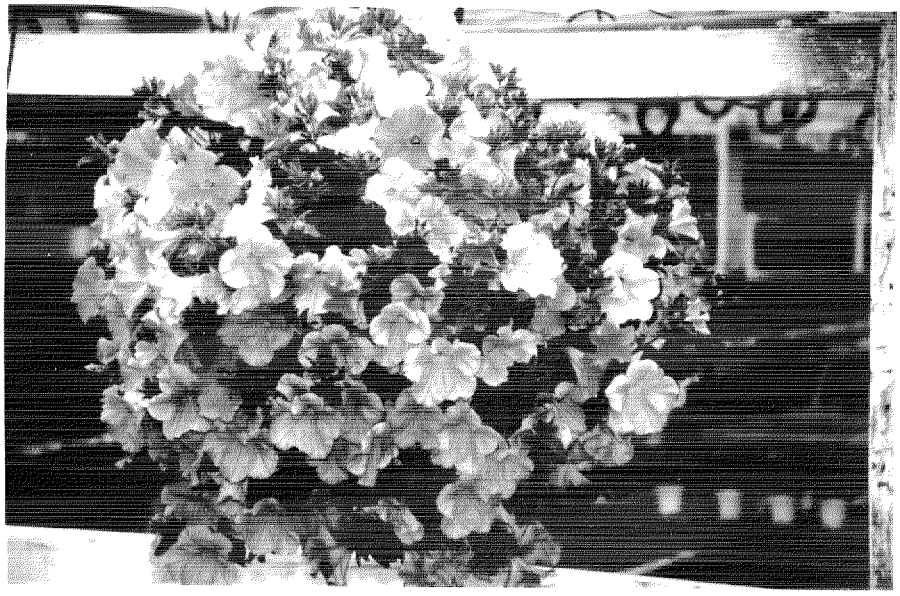

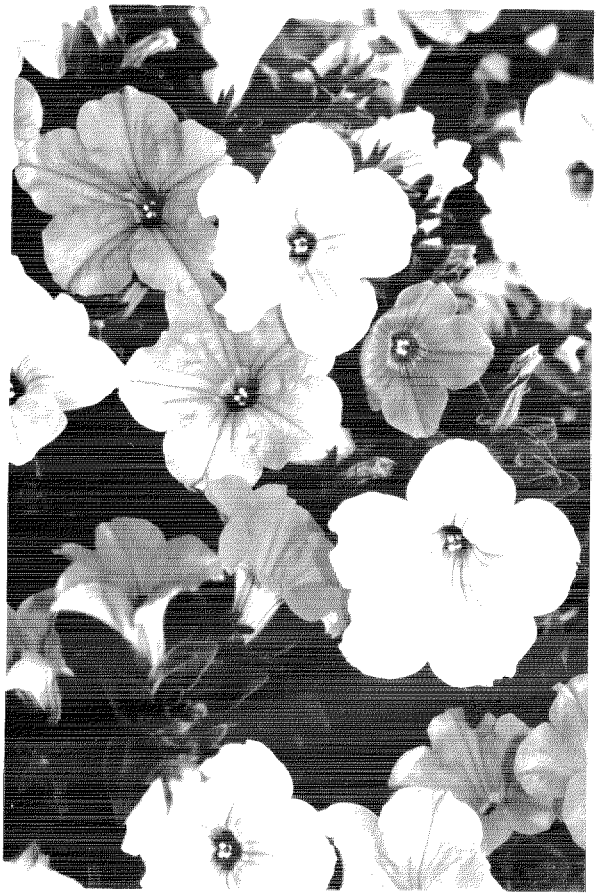

* * * * *